United States Patent
Nagayama (10) Patent No.: US 7,332,284 B2
(45) Date of Patent: Feb. 19, 2008

(54) METHOD OF DETERMINING BASE SEQUENCE OF DNA OR RNA USING HEAVY ELEMENT LABELING AND IMAGING BY TRANSMISSION ELECTRON MICROSCOPY

(75) Inventor: Kuniaki Nagayama, Aichi Prefecture (JP)

(73) Assignee: Nagayama IP Holdings LLC, New York, NY (US)

( * ) Notice: Subject to any disclaimer, the term of this patent is extended or adjusted under 35 U.S.C. 154(b) by 0 days.

(21) Appl. No.: 11/130,801

(22) Filed: May 16, 2005

(65) Prior Publication Data

US 2005/0244875 A1 Nov. 3, 2005

Related U.S. Application Data

(63) Continuation of application No. 09/992,538, filed on Nov. 19, 2001, now abandoned.

(51) Int. Cl.
*C12Q 1/68* (2006.01)
*C12M 1/34* (2006.01)
*C07H 21/04* (2006.01)

(52) U.S. Cl. .............. 435/6; 435/287.2; 536/23.1

(58) Field of Classification Search ............ 435/6, 435/287.2, 91.1, 183; 436/94, 800; 536/23.1
See application file for complete search history.

(56) References Cited

U.S. PATENT DOCUMENTS 5,470,707 A * 11/1995 Sasaki et al. ............ 435/6
5,800,992 A * 9/1998 Fodor et al. ............ 435/6
2002/0011566 A1 1/2002 Nagayama et al. ........ 250/311

FOREIGN PATENT DOCUMENTS

| JP | 11258057 | 9/1999 |
| WO | WO 99/09217 | 2/1999 |
| WO | WO 00/06770 | 2/2000 |

OTHER PUBLICATIONS

"Base Sequence Determination in Nucleic Acids With the Electron Microscope, III. Chemistry and Microscopy of Guanine-Labeled DNA", Evangelos N. Moudrianakis and Michael Beer, *Proc. Natl. Acad. Sci. USA*, vol. 53, pp. 564-571 (1965).
"Visualization of DNA by Scanning Probe Microscopy" (in Japanese), Hiroyuki Tanaka et al., *Biological Physics*, vol. 40, No. 5, pp. 336-340, (2000).
"A Study of Specific Pair Bonding of Nucleic Acid Bases by Ultra-Red Spectroscopy" (in Japanese), Yoshimasa Kyogoku, *The Field of Chemistry*, vol. 22, No. 4, pp. 364-374 (1968).

* cited by examiner

*Primary Examiner*—Bradley L. Sisson
(74) *Attorney, Agent, or Firm*—Fish & Richardson P.C.

(57) ABSTRACT

Novel DNA sequence determination method and DNA sequencer system providing a sequencing speed $10^3$ to $10^4$ times faster than the current DNA sequencing speed ($10^5$ bases per day with a lane at maximum) of the existing DNA sequencer based on electrophoresis. The method includes the step of discriminating base-specific labels of heavy elements using a magnified image of elongated single-chain DNA or RNA produced by a transmission electron microscope (TEM). The DNA sequencer system uses this method. The invention provides a DNA sequencing speed that is higher than the existing speed by 3 or 4 orders of magnitude.

1 Claim, 2 Drawing Sheets

METHOD OF DETERMINING BASE SEQUENCE OF DNA OR RNA USING HEAVY ELEMENT LABELING AND IMAGING BY TRANSMISSION ELECTRON MICROSCOPY

This application is a continuation of U.S. application Ser. No. 09/992,538, filed Nov. 19, 2001, now abandoned, which claims priority to Japanese application serial no. 2000-351844, filed Nov. 17, 2000, all of which are hereby incorporated by reference.

BACKGROUND OF THE INVENTION

1. Field of the Invention

The present invention relates to a method and apparatus for determining the base sequence of a DNA or the like of biological or non-biological origin and, more particularly, to a so-called ultrahigh-speed DNA sequencer used to sequence the bases of DNA or the like at high speed. The sequencer consists mainly of a transmission electron microscope (TEM) for producing magnified visible images of DNA molecules and parts and involving specimen adjustment, TEM imaging, and image analysis.

2. Description of the Related Art

The prior art DNA base sequencing is a wet chemistry technique consisting principally of DNA length separation making use of electrophoresis. This technique is based on DNA cutting, fluorescence labeling, and reading of a separation pattern or electrophoresis pattern. All the sequencing techniques have been developed based on this key technique. In recent years, it was said that Celera Genomics, U.S., successfully sequenced $3 \times 10^{10}$ DNA bases (human genome from one person) in one year. This achievement was made by operating 200 DNA sequencers each having tens of electrophoresis lanes in parallel. Although this achievement was accomplished by ultra-paralleling of machines of the same construction, the analysis speed of each electrophoresis lane is not so high, because the separation efficiency of electrophoresis is low. Today, it is considered that $10^4$ bases at most can be sequenced with one lane per day. The efficiency of DNA electrophoresis is improved by shortening the electrophoresis distance and introducing microscopy. The target is ten times the present speed, i.e., $10^5$ bases with one lane per day. However, it is considered that this is the limit of this method. This speed directly determines the cost of determining the base sequence. Currently, the cost is estimated to be about 10 yen per base. Accordingly, the present cost of sequencing the genome of a person is estimated to be $3 \times 10^{10}$ bases$\times$10 yen/base=$3 \times 10^{11}$ yen=30 billion yen (about 250 million dollars).

Under these circumstances, the present cost is so high that the genome information industry cannot emerge. It is essential to develop a method of reducing the cost by three to four orders of magnitude. In an attempt to achieve this, various methods have been proposed. One known method is to aim at a certain genome DNA, and its existence is probabilistically known like DNA chips that are already available on the market. Another known method uses a scanning probe microscope, especially a scanning tunneling microscope, for producing magnified images of DNA molecules. This permits one to read base sequences (for example, *Biological Physics* (in Japanese), Hiroyuki Tanaka et al., Vol. 40, No. 5, pp. 336-340, 2000). However, the former technique has the problem that the accuracy is low; intrinsically, it is not a technique for sequencing unknown DNAs. The latter method has the problem that the data throughput is low, which is a limitation of scanning. In this way, these methods do not excel the existing electrophoresis.

Retrospectively speaking, various procedures were attempted in the 1960s when the existing DNA sequencer was not yet invented by Gilbert and Sanger. Among them, electron microscopy was considered to be most promising because of its high spatial resolution. Researches were conducted in wide application ranging from biology to physics. However, it has been difficult, even using electron microscopy, to determine the double-helical DNA sequence. Computer simulation of TEM images of DNA reveals that the four bases, or adenine(A), thymine(T), guanine(G), and cytosine(C), cannot be distinguished from each other even at a spatial resolution of 0.05 nm, for example. In contrast with this, use of single-chain DNA yields many advantages. That is, i) the spacing (about 0.7 nm) between the successive bases when elongated is twice as wide as the spacing of double-helical DNA; ii) it is easy to label each base with a certain heavy atom; and iii) the method can be applied to RNA sequencing, as well as to DNA sequencing.

As a pioneer researcher making good use of these advantages, Evangelos N. Moudrianakis et al. attempted a method of labeling an organic substance (diazotized 2-amino-p-benzene disulfonic acid) with heavy uranium atoms by selectively bonding this organic substance to guanine(G) bases and labeling active bases (two sulfonic acids) of the organic substance with the heavy uranium atoms (*Proc. Natl. Acad. Sci. USA,* Vol. 53, pp. 564-571 (1965)). That is, if a TEM capable of resolving one uranium atom is used, base G can be identified from a pair of uranium atoms.

However, this method has not functioned as anticipated. One reason is that the guanine-specific bonding of organic substances has a problem. Another reason is that the TEM used at that time had not sufficient capability to identify a single uranium atom. It is considered that this poor capability arises not from low spatial resolution but from low image contrast; a single atom cannot be distinguished from noise coming from a carbon film or polymeric film that is a specimen support substrate, or background. It seems that the results were all artifacts.

As described thus far, the DNA sequencing speed will likely not exceed $10^5$ bases per lane per day as long as a DNA sequencer based on the prior art electrophoresis is used. With the existing method, it takes about one year to read the genome of a person, and the cost is about 250 million dollars. It is required that the genome be read in one week at about 1 million dollars. That is, it is required that the genome be read at ultrahigh speed much more economically. This will permit the genome information industry to emerge. For this purpose, development of an epoch-making, ultrahigh-speed DNA sequencer is essential.

To determine the base sequence of DNA at ultrahigh speed, it is essential to develop a measuring method for extracting a large amount of primary data about the sequence at ultrahigh speed. The TEM is considered to be the means that satisfies this requirement best today, because the instrument provides a magnification of one million and offers two-dimensional images. However, in view of the history of failures occurring more than thirty years ago, novel means including elongation of single-chain DNA, labeling of bases on a single-chain DNA with specific heavy elements, a high-resolution and high-contrast TEM capable of discriminating heavy elements, and an image analysis system for determining DNA sequences are required.

We have variously discussed the foregoing items and completed a novel system for determining the sequence of bases by integrating the above-described methods and instruments. The novel system does not use electrophoresis but is based on direct observation through a TEM.

SUMMARY OF THE INVENTION

It is an object of the present invention to provide a method of determining the base sequence of DNA or RNA by enabling base discrimination using a transmission electron microscope (TEM).

It is another object of the present invention to provide a novel DNA sequencer using this method.

In particular, the method of determining the base sequence of DNA or RNA (hereinafter simply referred to as "DNA") in accordance with the present invention discriminates base-specific labels of heavy elements on DNA, using a magnified image of elongated single-chain DNA produced by a TEM. The elongated single-chain DNA is obtained by modifying double-chain DNA collected from a cell or the like. On the other hand, with respect to RNA, it has intrinsically a single chain and, therefore, it can be used intact. Note that cDNA prepared using RNA as a template can also be used.

More specifically, this method comprises the steps of: (a) forming a support film on an electron microscope grid (TEM grid or EM grid), the support film holding the elongated single-chain DNA prepared in this way; (b) treating each base of the elongated single-chain DNA on the support film formed on the TEM grid with a base derivative containing a heavy atom or atoms to form base pairs at the bases of the elongated single-chain DNA, thus forming base-specific labels of heavy elements; and (c) producing a magnified image of the base-specific labels of heavy elements to permit one to distinguish the labels from each other. This sequence of operations is characterized in that it further includes the step (d) of reading the produced magnified image and sequencing the DNA by computer image analysis. At this time, it is adequate to use a high-density, low-noise, recording medium with a wide dynamic range as a recording medium for recording the magnified image produced by the electron microscope. Examples of such a recording medium include CCD and IP (imaging plate).

During image analysis, a further magnified image is taken while tilting the same specimen to remove the overlap of base-specific labels of heavy elements at intersecting sites to permit sequencing of even a single-chain DNA having intersecting chain portions. In this way, depth information is obtained. A process step for producing an image in which the overlap has been removed is added. Consequently, more accurate DNA sequence analysis is enabled.

A phase-contrast electron microscope or complex electron microscope is preferable in terms of contrast as the TEM used in the present invention. The support film that holds single-chain DNA is a film on which DNA is held. A specimen for TEM measurement is prepared by transferring this support film to the TEM grid. Protein denatured film matrix is especially desirable as this support film. Desirable proteins include natural proteins (e.g., albumin and casein) and artificial proteins (e.g., polylysine).

The support film for holding such elongated single-chain DNA is obtained by making use of rapid elongation of a DNA solution on a water surface. In particular, available methods include the LB (Langmuir-Blodgett) film method using a clean water surface, the vacuum spraying method consisting of spraying a DNA aqueous solution into vacuum.

In the present invention, base-specific labels of heavy elements on single-chain DNA or RNA to be sequenced are formed by forming any base pair of A-U*, T-A*, G-C*, C-G*, U-A* that are created by causing bases (i.e., adenine (A), thymine(T), guanine(G), and cytosine(C)) on single-chain DNA or bases (i.e., adenine(A), uracil(U), guanine(G), and cytosine(C)) on RNA to pair with bases labeled with heavy elements (i.e., adenine*(A*), uracil*(U*), guanine* (G*), and cytosine*(C*)). Note that * indicates labeling with a heavy element or elements.

Preferably, the above-described base derivatives containing heavy elements for forming such base-specific labels of heavy elements are bases labeled with heavy elements that can be discriminated from each other using a TEM. The heavy element with which such a base is labeled is preferably made of a heavy element complex that is bonded to the base. This heavy element complex should contain an element with a large atomic number. Generally, the complex contains a metal atom such as a heavy metal element.

In cases of adenine(A) and guanine(G), the site at which the substitutive base containing such a heavy element complex and the base are bonded is an imine group at 7- and/or 9-positions. In cases of uracil(U) and cytosine(C), the site is an imine group at 1-position because they do not affect the specific affinity between bases.

The heavy element used in the heavy element complex used in accordance with the present invention should be an element with a large atomic number that can be discerned using a TEM. Generally, metal elements with atomic numbers of greater than 25 are desirable. To permit distinguishment using a TEM, used metal elements preferably have atomic numbers that are spaced apart from each other by 15 or more. To obtain four kinds of heavy element complexes, four kinds of metal elements satisfying the above-described conditions are combined and used. Examples of combinations of such metal elements include "$_{78}$Pt, $_{63}$Eu, $_{46}$Pd, $_{27}$Co", "$_{92}$U, $_{76}$Os, $_{46}$Pd, $_{26}$Fe", "$_{80}$Hg, $_{64}$Gd, $_{48}$Cd, $_{30}$Zn", and "$_{89}$Ac, $_{74}$W, $_{42}$Mo, $_{25}$Mn", it being noted that the subscripts indicate atomic numbers. No limitations are imposed on what metal is used for what base. However, if a base with high frequency is combined with a lighter element or if a base with low frequency is combined with a heavier element, mutual interference can be generally reduced with desirable results. Examples of these combinations include "adenine-Pd, guanine-Pt, cytosine-Eu, uracil-Co" and "adenine-Zn, guanine-Hg, cytosine-Gd, uracil-Cd".

The heavy element complex used in the present invention is not limited to heavy element complexes where each molecule includes one metal atom. A complex including plural metal atoms can also be used. The use of these complexes is more desirable in terms of discrimination between elements or atoms and discrimination of signal from noise. One example of such complexes including plural metal atoms is a disubstituted heavy element complex in which one molecule contains two metal atoms. Another example is a trisubstituted complex containing three metal atoms. A further example is an iron-sulfur cluster-metal complex including four metal atoms. The atoms included in one complex may be similar or dissimilar metal elements.

For the discrimination of bases based on the total atomic number, the partial substitution of bases by heavy halogen atoms, such as iodide and bromide, can be used, but the high dose condition employed in this proposal may destroy their chemical bonds and force them to evaporate.

To secure higher solubility with respect to an organic solvent, a base labeled with a heavy element (A*, U*, G*, or C*) that is used for the above-described labeling may be partially substituted by at least one substituent group selected from the group consisting of alkyl groups, cyclohexyl groups, halogen groups, phenyl groups, and phenol groups. In the case of adenine(A), these substituent groups substitute the bases at the 2- and/or 8-positions. In the case of guanine(G), the substituent group substitutes the base at the 8-position. In cases of uracil(U) and cytosine(C), the substituent groups substitute the bases at the 5- and/or 6-positions. Where two substituent groups are coupled together, these substituent groups may be similar or dissimilar in kind.

To further enhance the selectivity of base-pair bonding for forming more specific bonding, these heavy element-labeled bases (A*, U*, G*, C*) are partially substituted by at least one substituent group selected from the group consisting of halogen groups and amino groups. In the case of adenine(A), these substituent groups substitute bases at the 2- and/or 8-positions. In the case of guanine(G), the substituent group substitutes the base at the 8-position. In the cases of uracil (U) and cytosine(C), the substituent groups substitute the bases at the 5- and/or 6-positions. Where two substituent groups are coupled together, these substituent groups may be similar or dissimilar in kind.

In the present invention, base pairs with heavy element-labeled bases that are base derivatives including the aforementioned heavy elements are preferably formed in an organic solvent, preferably in an organic solvent having a dielectric constant of less than 10. Among organic solvents having dielectric constants of less than 10, chloroform, heptane, cyclohexane, carbon tetrachloride, acetonitrile, aniline, ethyl amine, cresol, acetic acid, trichloroacetic acid, dimethyl ether, diethyl ether, toluene, toluidine, benzylamine, phenol, decanol, benzene, quinoline, morpholine, dimethyl amine, chlorobenzene, dichloromethane, dichloroethylene, tetrahydrofuran, trichloroethylene, dichlorobenzene, fluorobenzene, bromobenzene, pentanol, siloxane, and glyceride are desirable. A base derivative such as a heavy element-labeled base is dissolved in a solvent including at least one organic solvent selected from these organic solvents. DNA on the support film is treated with the resulting solution, and base pairs are formed. Thus, a base-specific label of heavy element is obtained. This assures base-specific bonding.

The TEM that is a key apparatus in embodying the base sequencing method in accordance with the present invention is preferably equipped with a tilt imaging system to obtain images from which overlap of crossing portions of chain on the TEM image is removed, in order to permit sequencing of even single-chain DNA or RNA having crossing chain portions on the produced TEM image during DNA sequence analysis. Furthermore, the phase-contrast electron microscope or complex electron microscope of transmission type is preferably loaded with software for TEM analysis for discriminating heavy elements. When elements are distinguished using this software, the resulting signal intensity is used as a basis for quantitative measurement.

Additionally, the present invention provides a DNA sequencer having a TEM for discriminating base-specific labels of heavy elements and an analyzer for sequencing bases of DNA or RNA by image analysis of a magnified image produced by the TEM. The labels form base pairs with bases on DNA of interest and are visualized. A different heavy element is used as a label for each different base. Thus, the kinds of the bases forming base pairs are discerned. Consequently, the DNA sequence of interest can be directly read.

Other objects and features of the invention will appear in the course of the description thereof, which follows.

DESCRIPTION OF THE PREFERRED EMBODIMENTS

The present invention provides a DNA sequencer system including a high-resolution and high-contrast transmission electron microscope and an image analysis system. The sequencer system discriminates between base-specific labels of heavy elements, using a magnified image of elongated single-chain DNA or RNA produced by the transmission electron microscope (TEM). Thus, DNA or RNA sequence is determined at high speed. The sequencer system utilizes elongation of single-chain DNA and base-specific labeling of bases on single-chain DNA with heavy elements. The high-resolution and high-contrast TEM permits one to distinguish between the kinds of heavy elements. The image analysis system determines the sequence of DNA.

Figure 1:
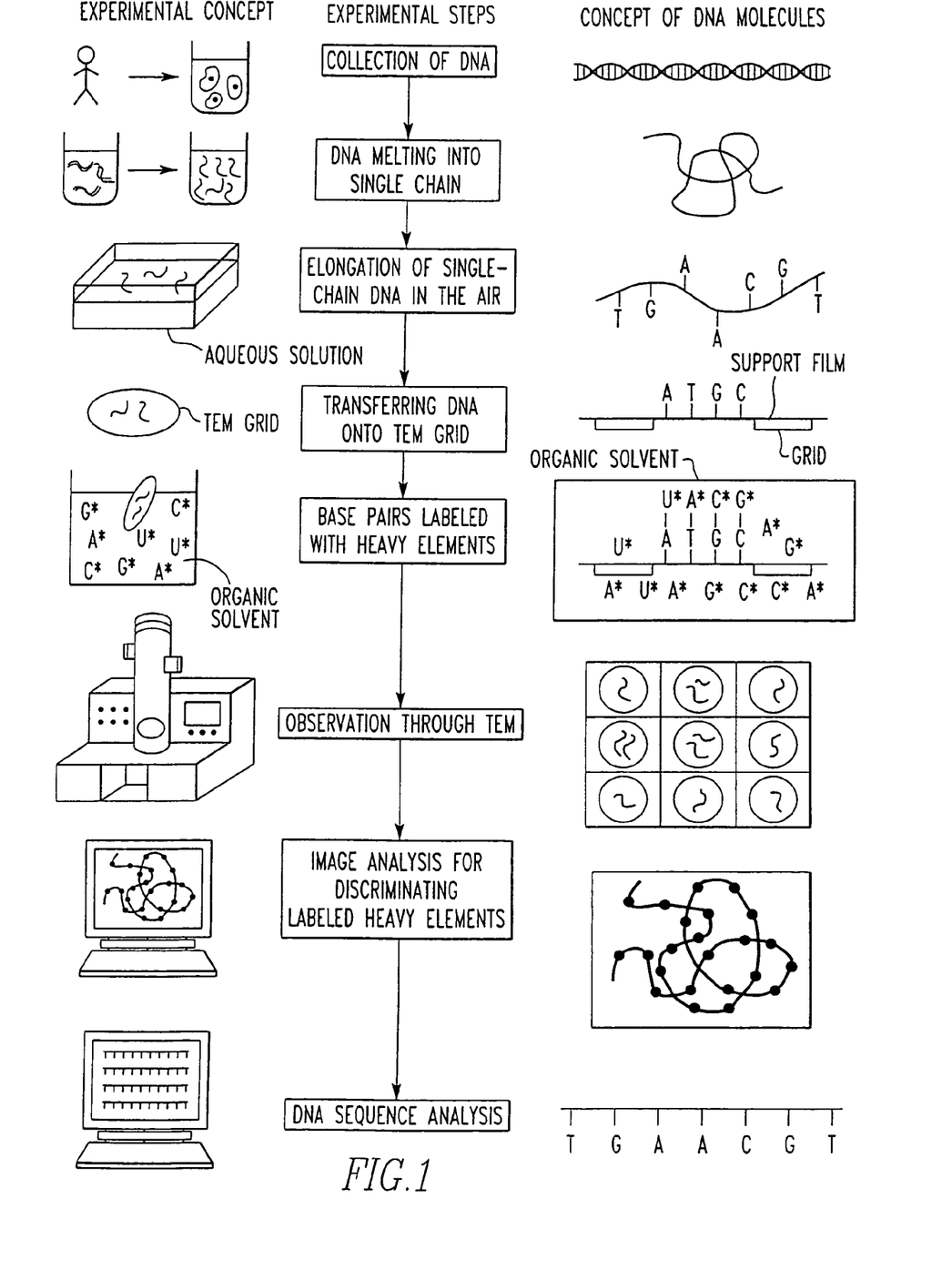
FIG. 1 is a conceptual diagram illustrating the whole of a DNA sequencer system in accordance with the present invention.

The whole DNA sequencer system in accordance with the present invention is conceptually shown in FIG. 1, which illustrates successive experimental steps. In this figure, the experimental concept and the concept of corresponding DNA molecules are summarized. Items to be processed in the successive steps of FIG. 1 and an embodiment of the present invention are described in detail below. Collection of DNA and a DNA melting step for melting and modifying the DNA to obtain a single-chain DNA, as shown in FIG. 1, are achieved by well-known techniques.

1) The TEM Itself

It is essential that the TEM used in the present invention have sufficient contrast and resolution to make a quantitative elemental analysis of one atom of a heavy element with an atomic number equal to or greater than 25. Different elements are distinguished by making use of differences in electron scattering intensity dependent on atomic numbers. Therefore, it is required that signal intensities from two elements with atomic numbers spaced apart from each other by at least 15 be quantitatively detected so that the two elements can be distinguished on a TEM image.

In view of the foregoing, the present invention makes use of the following TEM. The TEM should be capable of identifying the element of one atom or the elements of an atomic cluster made of 3 to 5 atoms. This instrument can be obtained by enhancing a commercially available TEM as follows. This enhanced TEM is used in the present invention.

i) Phase-Contrast Electron Microscope

The most powerful method of recovering the contrast without sacrificing the resolution and forming a quantitative TEM image that permits the atomic numbers of atoms to be discriminated is to use a phase-contrast electron microscope. The phase-contrast electron microscope is achieved by inserting a Zernike phase plate into a location close to the focal plane behind the objective lens (Japanese Patent Application No. 2000-085493). However, to achieve a high resolution (0.2 to 0.3 nm) permitting discrimination between heavy elements, the TEM must have low spherical aberration and chromatic aberration and thus have high resolution limit. A high-resolution and high-contrast TEM that permits insertion of a phase plate and is capable of discriminating between individual atomic elements needs a high voltage of more than 300 kV. In the case of discrimination between element clusters each made up of 3 to 5 atoms, a 100 kV TEM can also be used.

ii) Complex Electron Microscope

If a phase-contrast electron microscope cannot achieve a resolution of 0.2 to 0.3 nm, the resolution can be improved by redesigning the instrument as a complex electron microscope. Complex electron microscopy is a method of combining a phase-contrast electron microscope and a normal TEM (Japanese Patent Publication No. 11-258057). For example, a complex electron microscope image consisting of a real number component signal and an imaginary number component signal is obtained by detecting the real number component TEM image of a specimen and the imaginary number component TEM image produced by phase-shifting only electron waves transmitted through the specimen by $\pi/2$ and taking the complex sum of the real number component TEM image and the imaginary number component TEM image. However, the analysis is slightly more complex than in phase-contrast electron microscopy.

iii) Cryogenic Specimen Stage

Another method of improving the contrast is to increase the permissible electron dose by making use of a cryogenic specimen stage. This method can be implemented independent of the methods i) and ii) described above. Increase in the electron dose increases the signal intensity at a higher rate than noise, thus improving the contrast.

As described thus far, a phase-contrast electron microscope or complex electron microscope is used as a TEM. If necessary, the specimen stage is kept at a cryogenic temperature. In consequence, a magnified image having high resolution and contrast can be obtained.

2) Robust Thin Film for Holding Single-Chain DNA

When elongated, the space between bases is as long as 0.7 nm. Therefore, it is easy to variously chemically modify bases. Also, milder requirements are imposed on the resolution of the TEM. However, unique contrivances are required in making the DNA of interest have a single chain, elongating it, and holding it on a specimen support (TEM grid or EM grid) for the TEM.

Even if the TEM has the capability of identifying one atom of a heavy element under ideal conditions, the following two noise problems must be solved in exhibiting the capability in practice: i) background shot noise, and ii) fog arising from the specimen support base. The former problem can be reduced by increasing the permissible electron beam dose. With respect to the latter problem, the support base should be thinned to such an extent that the electron beam illumination does not destroy the support base.

Therefore, the problems i) and ii) can be solved by providing a thin film that firmly holds DNA, is robust enough to withstand intense electron beam irradiation, and is made of a light element having small electron beam scattering power.

On the other hand, in morphological research using a TEM, an electron beam dose that does not damage the morphology of a specimen of interest has been defined as an allowable amount. In the present invention, however, only labeling heavy elements are observed and so the morphology of an organic substance such as DNA is not important. Rather, illumination of a strong electron beam exceeding the tolerable dose for the organic substance is desirable to obtain high contrast. The object is achieved even if the morphology is destroyed or the organic part of substances is lost by evaporation, as long as heavy elements necessary for sequencing are preserved retaining their relative positions. The major reason to use metal elements for the base sequencing lies in their superior property of the positional preservation compared with halogens. The holding film itself must be robust. Carbon thin film and aluminum thin film have been already known as robust films for holding DNA. However, these films produce strong background fog and also tend to decrease the contrast of labeling heavy elements bonded as base pairs. More desirable results are obtained by making use of organic films such as the LB films made of lipids and protein denatured films which have smaller electron beam scattering power and hence prevent fogging of the image due to the support plate (i.e., producing less fog).

The organic thin film holding DNA is transferred to a carbon film provided with numerous holes. The film is positioned so as to cover the holes in the carbon film, and acts as a support base for DNA.

3) Base-Specific Labeling With Heavy Element Using Specific Base-Pair Bonding

The method of directly and base-specifically labeling bases on single-chain DNA with heavy elements that can be discerned using a TEM has the problem of base selectivity as mentioned previously. The present labeling method has solved this problem by using naturally occurring specific base-pair bonding. The naturally occurring DNA has the function of transferring genetic information using specific base pairs of A-T and G-C.

It is generally considered that the specificity of this pair bonding is caused by complementary hydrogen bonding. However, if monomers of A, T, G, and C are mixed, such specific and selective pair bonding is not created in an aqueous solution. Water molecules existing in large amounts compete with hydrogen bonding and so base-pair bonding weakens. Also, the specificity disappears. However, if the environment is apart from water, the specificity of base pairs owing to hydrogen bonding is recovered. Especially, in an organic solvent of low polarity, specific pair bonding appears (e.g., Yoshimasa Kyogoku, "The Field of Chemistry" (in Japanese), Vol. 22, No. 4, pp. 364-374 (1968)). Although this fact was known more than 30 years ago, it has not been used as a method of specifically labeling bases on DNA.

The present labeling method utilizes these specific base pairs appearing in an organic solvent. To enhance the efficiency, each base is chemically modified in the following three ways: i) each base is modified with a heavy element complex bonding and/or a heavy element substitution to facilitate discrimination using a TEM; ii) modification for dissolubility into an organic solvent to facilitate formation of base-pair bonding; and iii) modification for enhancing the specificity of the formed base-pair bonding.

In the present invention, an organic thin film that supports single-chain DNA and is in a dry state is dipped into an organic solvent including bases labeled with heavy elements to form complementary base pairs with bases on the single-chain DNA. In this method, the chemical species of base monomers labeled with heavy elements and the kind of the organic solvent are important.

i) Selection of Base Species

Some base species which selectively form strong pair bonding with A, T, G, and C of DNA are known (Yoshimasa Kyogoku, "The Field of Chemistry" (in Japanese), Vol. 22, No. 4, pp. 364-374 (1968)). Among them, four bases of adenine(A), uracil(U), guanine(G), and cytosine(C) are selected as fundamental base species (monomers) for the high-speed DNA sequencer in accordance with the present invention because of easiness of modification and complementary base pair selectivity. U, A, G, and C are made to form pair bonding with A, T, C, and G, respectively, on single-chain DNA. In the present invention, uracil(U) whose methyl group is not substituted is adopted because it has wider variousness than thymine(T).

Chemical Formula 1 adenine A uracil U guanine G cytosine C

The following Watson-Crick model is assumed to be base pairs. However, various contrivances are necessary to enhance the selectivity as described below.

Chemical Formula 2

U A

C G ii) Improvement of Base Pair Selectivity

For example, G forms pairs with other than C. That is, G-G, G-A, G-U, etc., are erroneous base pairs. Improvement of selectivity of base pairs A-U and G-C depends on chemical design for minimizing the possibility of such errors. Furthermore, another type of base pairing (Hoogsteen base pairing) different from the Watson-Crick model exists, if they are base pairs of A-U and G-C as shown below.

Chemical Formula 3

U A

To prevent this, four bases A, U, G, and C are modified with halogens (e.g., Br and I), methyl groups, ethyl groups, alkyl groups (such as cyclohexyl groups), amino groups, or the like. Modification sites can be 2- and 8-positions for A, 8-position for G, and 5- and 6-positions for U and C. Halogenation of A and G at 8-position, amination of A at 2-position, and halogenation of U and C at 5-position intensify pair bonding and enhance the selectivity.

Hoogsteen base pairing is prevented as follows. With respect to A and G, alkylation at 8-position is desirable. Intrinsically, C produces a weak Hoogsteen bond with G and so produces no problems. However, with respect to U, Hoogsteen base pairing cannot be prevented merely by base modification.

As such compounds, examples of adenine and uracil include 8-bromopurine, 2,6-diaminopurine, 5-bromouracil, 5-iodouracil, and 5-alkyluracil. In the present invention, uracil is adopted. Introducing a methyl group into 5-position of uracil to enhance the selectivity of pair coupling gives rise to nothing other than thymine. Accordingly, thymine derivatives are also embraced in the uracil derivatives in accordance with the present invention.

iii) Dissolubility Into Organic Solvent

Dissolubility into an organic solvent is also a requirement. In the same way as improvement of selectivity, it is considered that modifications of A at 2- and 8-positions, G at 8-position, and U, C at 5- and 6-positions are conceivable. Halogenation and alkylation for improving the selectivity of pair bonding are advantageous for dissolubility into organic solvents. Modification with a highly hydrophobic alkyl group at a position where base-pair bonding is not hindered is desirable. For A and G, 8-position is desirable. For U and C, 6-position is preferable. Examples of the modifying group include ethyl groups, propyl groups, and cyclohexyl groups. These compounds are similar to the compounds listed in ii) above except for amino groups. It can be seen that halogen and alkyl groups contribute to both improvement of dissolubility into organic solvents and improvement of the selectivity of pair bonding formation. Improvement of dissolubility into organic solvents can also be accomplished by introducing an alkyl group or the like to nitrogen atom at 7- or 9-position of A or G and to nitrogen atom at 1-position of U or C. In addition, a heavy element complex that is used for labeling may promote dissolubility into an organic solvent depending on the design.

iv) Selection of Label of Heavy Element

A base derivative for forming a base-specific label of heavy element in accordance with the present invention is preferably labeled with a heavy element complex because it is dissoluble to organic solvents and resistive to the mass loss event due to electron bombardment. Such heavy element complexes are anchored as covalent bond to nitrogen atom at 7- or 9-position for A and G and to nitrogen atom at 1-position for U and C. In this way, bases labeled with heavy elements are obtained. Any desired substance can be used as such heavy element complexes as long as it exists stably. Examples of such complexes include amine complexes of various metals, benzene complexes, metallocene complexes, olefin complexes, and many other complexes. When a heavy element complex is bonded to a base, it can be a heavy element complex obtained by coordinating a metal element directly to nitrogen within a base. Furthermore, a heavy element complex may be bonded to nitrogen within a base via a so-called linker or adapter, such as a polymethylene chain or polyoxyalkylene chain.

On the other hand, a metal element used as a heavy element complex needs an electron scattering intensity that is strong enough to be discerned as one metal element by a TEM. At present, metal elements with atomic numbers of greater than 25, preferably greater than 30, fulfill this requirement. Since metal elements are distinguished according to electron scattering intensity originating from each metal, the atomic numbers of used metal elements should be spaced apart by at least 15, preferably more than 20. Four kinds of metal elements used in this way are employed to label bases (A, U, G, C) with metal elements. Any arbitrary combination of the used metal elements may be used. Desirable combinations include "Pt, Eu, Pd, Co", "U, Os, Pd, Fe", "Hg, Gd, Cd, Zn", and "Ac, W, Mo, Mn". Where labeled bases A*, U*, G*, and C* are prepared, any arbitrary heavy element can be used to label any arbitrary base.

The bases labeled with heavy elements obtained as described above are base derivatives including heavy elements, the base derivatives having chemical structures in which heavy element complexes having the four kinds of metals are bonded to bases. The base derivatives are used as a treatment agent for forming base-specific labels of heavy elements on the desired DNA. Specific examples of heavy element-labeled bases each including a complex in which one heavy atom is coordinated are as follows. These compounds are shown to be pair bonded to bases on DNA.

Chemical Formula 4

In these examples, A* (labeling with palladium with atomic number 46), C* (labeling with europium with atomic number 63), G* (labeling with platinum with atomic number 78), and U* (labeling with cobalt with atomic number 27) selectively form pair bonding with bases T, G, C, and A on DNA. Heavy elements on them act as reporters that can be discriminated using a TEM. Where such a base labeled with a heavy element is used, if the spot of platinum atom is discerned on a TEM image, the corresponding base of single-chain DNA can be distinguished from C. The other three bases can be similarly determined by discerning the spots of their respective metal atoms and make discriminations. The above examples are the simplest base-metal complex bonding and base-organic metal complex bonding. In these cases, only one heavy metal element is included. Lying at the anchor position of the heavy element complex is nitrogen. In the cases of A and G, the nitrogen is either at 7-position or at 9-position. The shown structural formula gives only the case of 7-position.

Of course, it is also possible to make bonds at both 7- and 9-positions rather than either 7-position or 9-position. In this case, the number of heavy atoms is increased. The resolution and contrast of the TEM image are enhanced accordingly. Also, better discrimination is enabled.

If element clusters are used for labeling with heavy elements, the image contrast is enhanced. Consequently, the sensitivity and reliability in discriminating between elements are improved greatly. Since the clusters are large, the required resolution can be made low. With a phase-contrast electron microscope with low voltage (e.g., 100 kV), DNA sequences can be visualized to a satisfactory extent.

The most promising candidates for such element clusters are naturally occurring iron-sulfur clusters and their metal substitutes. An iron-sulfur cluster is cubic (cubane). Iron and sulfur atoms are alternately coordinated at the eight apexes. Therefore, a cluster level consisting of four heavy atoms occurs. Clusters of such metal elements also exist as complexes. In the present invention, what are composed of a single metal including complexes and these clusters are referred to as "heavy element complexes" or simply as "complexes".

In nature, these heavy atoms are anchored to the main chain of protein via cysteine (Cys) introduced into protein as described below.

Intrinsically, these clusters are unstable in water. However, they are protected by proteins and stably exist in living bodies. Many proteins containing iron-sulfur clusters, such as ferredoxin and hydrogenase, are known. Generally, in an organic solvent, such clusters are stable in a bare state if not protected by proteins. Therefore, if these clusters can be anchored to bases directly or via appropriate adapters or linkers, then strong bases labeled with heavy element clusters are created.

Heavy elements forming these clusters are various heavy elements, in addition to iron with atomic number 26. For example, tungsten with atomic number 74, molybdenum with atomic number 42, and so on, are taken in stably. By combining these metals, a metal cluster including two iron atoms and two molybdenum atoms, for example, can be formed. In this way, heavy element cluster-labeled bases that can be discriminated by bases can be obtained by creating heavy element-sulfur clusters with different total atomic numbers (i.e., the sum of the atomic numbers of all constituent metal atoms; in the above case, the total atomic number=26×2+42×2=136).

v) Selection of Organic Solvent

When a base-specific label of heavy element is formed by treating elongated DNA on a support film with a base derivative containing the aforementioned heavy elements, the organic solvent used during the treatment affects the result greatly. In particular, from a viewpoint of base pair selectivity, nonpolar or low-polar organic solvents, such as carbon tetrachloride, cyclohexane, and benzene, are generally desirable. However, from a viewpoint of dissolubility, polar solvents, such as chloroform, toluene, aniline, and pentanol, are desirable. The used solvent is selected, taking account of these considerations. Where the aforementioned heavy element-labeled bases are used, examples of the solvent used in the present invention include chloroform, toluene, and carbon tetrachloride, though the used solvent may be varied according to the kind of base derivative containing heavy elements used for pair bonding.

Chemical formula 5

4) TEM Imaging and Image Analysis System

An image of single-chain DNA labeled with heavy elements and produced by the improved TEM is accepted as digital data into a computer, processed at high speed, and the base sequence is determined. Software dedicated for DNA sequence determination is loaded in a general-purpose graphics computer. TEM imaging and a system for analyzing the obtained magnified image are described below.

i) Imaging Process and Recording Medium

A recording medium used for image analysis needs to correspond to the magnified image produced by the TEM.

The total number of bases contained in a piece of elongated single-chain DNA visualized as a magnified TEM image is adjusted to about $10^5$. The TEM image is taken by an operation that takes about 10 seconds or so. If this is taken as the throughput of determination of base sequences, the efficiency is improved by about 4 orders of magnitude compared with the separation speed of $10^5$ bases per day in an electrophoresis lane.

It is assumed that one base occupies an area of 0.7 nm×0.7 nm within the TEM image. The spacing between bases on single-chain DNA gives a measure. If an allowance that is 10 times the occupied area is given to the TEM image for reliable discrimination between bases, then one frame of image has an actual area of $0.7 \times 0.7 \times 10 \times 10^5$ nm$^2 = (0.7 \times 10^3)^2$ nm$^2$. That is, a space of about 1 μm square is the field of view of the TEM. If each pixel is set to half the resolution (e.g., 1.5 nm), then the number of required pixels is $(0.7 \times 10^3$ nm/0.15 nm$)^2 \cong 2 \times 10^7$. Those of existing digital recording media which have corresponding numbers of pixels are CCDs and imaging plates (IPs). However, the size per pixel is preferably substantially equal to the pixel size of about 5 μm of high-resolution photographic film.

ii) Analysis of DNA Sequence of Crossing, Elongated Chain of DNA

The present analysis system is characterized in that it can analyze the sequence of single-chain DNA where the chain is bent and forms portions barely crossing each other, as well as a completely straight stretched a single-chain DNA. If the base spacing between chain portions close to an intersection is wide, bases can be discriminated based on the atomic number dependence intensity of the spot observed while tracing a single chain. Thus, the sequence can be determined. If no intersections are present, commercially available software can be used for analysis.

The problems are base discrimination at intersections and discrimination in the direction of depth. To solve these problems, the same sample is tilted at approximately 30° and another image is taken under this condition. In this way, depth information is obtained, and an image from which overlap has been removed is derived. Hence, two overlapping chemical elements can be discriminated. An analysis for performing this sequence of operations is the feature of the present system.

As described thus far, a base-specific label of a heavy element obtained by pair bonding using the heavy element-labeled base given in Chemical Formula 4 is derived. This label is subjected to complex processing using a complex electron microscope. Thus, the base is visualized. This is conceptually shown in FIG. 2.

Figure 2:
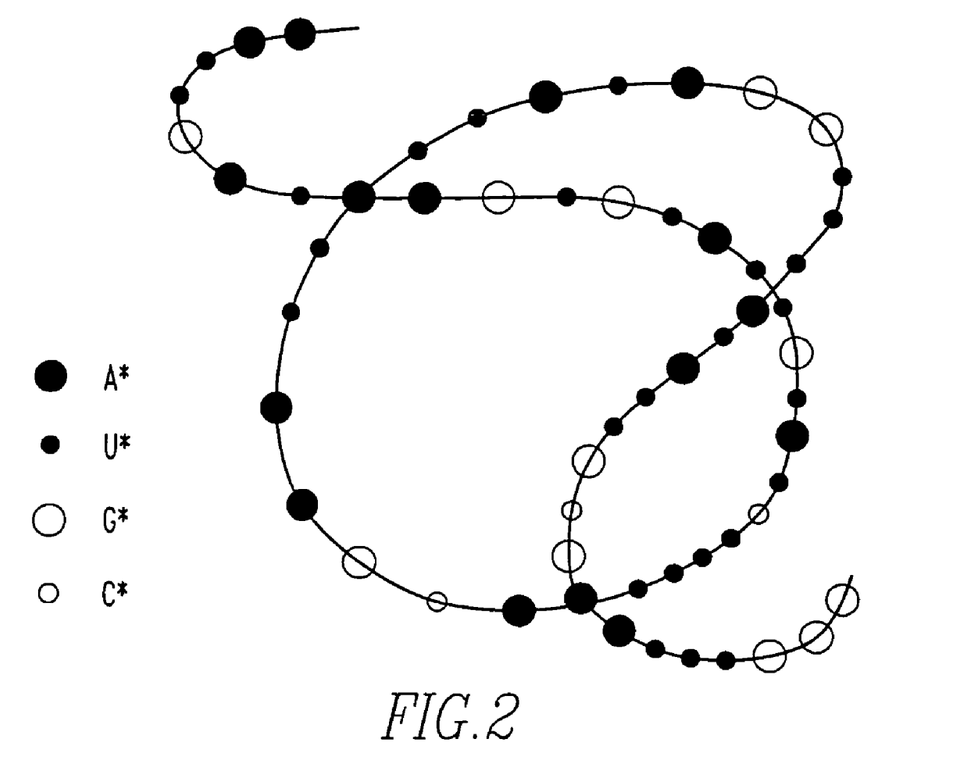
FIG. 2 is a conceptual diagram illustrating visualization of single-chain DNA, using the method and system in accordance with the present invention, and in which large black circles, small black circles, large white circles, and small white circles denote A*, U*, G*, and C*, respectively.

In a magnified image produced by a TEM, heavy elements pair-bonded to bases on DNA are discriminated according to their atomic numbers, i.e., differences in electron scattering intensity corresponding to their masses. That is, they are discriminated according to their image sizes.

To facilitate conceptual understanding, the image sizes are not correctly shown in FIG. 2, where large black circles, small black circles, large white circles, and small white circles denote A*, U*, G*, and C*, respectively. A DNA sequence of interest can be determined by discriminating pair-bonded, heavy element-labeled bases. That is, it can be seen from FIG. 2 that bases labeled with heavy elements are A*A*U*C*G*A* . . . when taken along the DNA from the left top position. Accordingly, it is determined that the original base sequence of DNA to be determined is TTAGCT . . .

The DNA base sequence can be determined by selectively modifying bases on a single-chain DNA with bases labeled with heavy elements and discriminating the heavy elements on a TEM image. This DNA base sequence analysis speed is higher than the speed of the existing sequence determination method using electrophoresis by 3 to 4 orders of magnitude.

Having thus described my invention with the detail and particularity required by the Patent Laws, what is desired protected by Letters Patent is set forth in the following claims.

What is claimed is:

1. A method of determining the sequence bases of a DNA or RNA, comprising the steps of:
   (a) providing a support film, on which an elongated single-chain DNA or RNA is held, on an electron microscope grid;
   (b) exposing the elongated single-chain DNA or RNA on the support film to a guanine derivative, an adenine derivative, a cytosine derivative, and a uracil derivative, each derivative containing a different heavy element label comprising a heavy element or elements
   (c) allowing the guanine derivative, the adenine derivative, the cytosine derivative, and the uracil derivative to form base pairs with the single-chain DNA or RNA in the presence of an organic solvent to form a base-specific labeled elongated single-chain DNA or RNA;
   (c) obtaining a magnified image of a portion of the base-specific heavy element labeled elongated single-chain DNA or RNA, wherein the portion of DNA or RNA does not cross itself using a transmission electron microscope and discriminating said base-specific labels of heavy elements using the obtained magnified image.

* * * * *